(12) United States Patent
Martin

(10) Patent No.: US 6,918,892 B2
(45) Date of Patent: Jul. 19, 2005

(54) INTRAOSSEOUS NEEDLE

(76) Inventor: Howard Martin, 11500 W. Hill Dr., Rockville, MD (US) 20852

( * ) Notice: Subject to any disclaimer, the term of this patent is extended or adjusted under 35 U.S.C. 154(b) by 0 days.

(21) Appl. No.: 10/830,704

(22) Filed: Apr. 23, 2004

(65) Prior Publication Data

US 2005/0065473 A1 Mar. 24, 2005

Related U.S. Application Data

(60) Provisional application No. 60/465,017, filed on Apr. 23, 2003.

(51) Int. Cl.[7] .............................. A61M 5/00; A61M 5/32
(52) U.S. Cl. ........................................ 604/239; 604/272
(58) Field of Search ................................. 604/272, 264, 604/218, 235, 239; 433/75, 89, 90

(56) References Cited

U.S. PATENT DOCUMENTS

| | | | | |
|---|---|---|---|---|
| 561,059 A | * | 5/1896 | Mitchel et al. ........ | 604/165.02 |
| 3,110,304 A | * | 11/1963 | Hartman ...................... | 600/200 |
| 5,531,694 A | * | 7/1996 | Clemens et al. ............ | 604/110 |
| 5,562,696 A | * | 10/1996 | Nobles et al. ............... | 606/185 |
| 5,688,224 A | * | 11/1997 | Forkey et al. ............... | 600/200 |
| 6,004,330 A | * | 12/1999 | Middleman et al. ........ | 606/127 |
| 6,077,248 A | * | 6/2000 | Zumschlinge ........... | 604/167.01 |
| 6,432,045 B2 | * | 8/2002 | Lemperle et al. ............ | 600/135 |
| 6,743,177 B2 | * | 6/2004 | Ito ............................... | 600/461 |
| 2003/0120154 A1 | * | 6/2003 | Sauer et al. ................. | 600/459 |

* cited by examiner

Primary Examiner—Sharon Kennedy
(74) Attorney, Agent, or Firm—Law Offices of Royal W. Craig

(57) ABSTRACT

An improved intraosseous injection system including an injection needle constructed of high strength metal to resist bending and buckling mounted within a protective and supportive sleeve. The sleeve includes a retractable cannula for additional protection and support of the needle and a measuring gauge for precise sighting alignment to properly locate the site for an effective anesthetic injection. The movement of the retractable cannula is limited by a stop which operates to position the needle at the correct depth of penetration for delivery of anesthetic to the most effective location.

20 Claims, 3 Drawing Sheets

INTRAOSSEOUS NEEDLE

CROSS-REFERENCE TO RELATED APPLICATIONS

The present application derives priority from U.S. Provisional Patent Application No. 60/465,017 for "IMPROVED INTRAOSSEOUS NEEDLE"; Filed: Apr. 23, 2003.

BACKGROUND OF THE INVENTION

1. Field of the Invention

The invention relates to improved intraosseous injection system and, more particularly, to a strengthened intraosseous needle with positioning gauge and a penetration limiting stop to obtain precise delivery of an anesthetic to the most effective site, in a patient's mouth, and reduce the pain associated with endodontic treatment.

2. Description of the Background

The administration of anesthetics is an important part of dentistry. The effective reduction of pain makes a patient comfortable and allows the dentist to operate with confidence. Pain control is more difficult when a diseased nerve is causing acute pain before the treatment has begun. This is often the situation in endodontic (root canal) therapy. Known injection techniques are typically used to achieve pulpal anesthesia, which normally alleviates the pain from the diseased nerve and allows the dentist to complete therapy without complications from excessive pain. However, there are situations where these known techniques are insufficient because either the patient has a low threshold for pain or for some other reason the anesthetic is not sufficiently effective to reduce the pain.

Usually, an anesthetic is injected into the lingual aspect of the mandibular ramus, using conduction anesthesia (the mandibular block). Due to variations in human bone structure, the effectiveness of this procedure depends, in part, on the location of the affected tooth. Mandibular block anesthesia is more likely to fail when the disease is present in a mandibular tooth as opposed to a maxillary tooth. The reduced failure rate in the maxilla is due to the thin cortical plate of the maxilla. The cortex of the mandible is much thicker. A study by Walton and Abbott showed incomplete anesthesia in 32% of maxillary teeth and 66% in mandibular teeth (Walton, R. and Abbott, B. "Periodontal Ligament Injection: A Clinical Evaluation", *Journal of the American Dental Association*, 1981; 103:571). A separate study by Malamad found that mandibular teeth were not effectively anesthetized 91% of the time (Malamad, S. "Teeth Requiring Supplemental Injections, [unpublished data] 1997). Infiltration anesthesia can be used for the maxilla and effectiveness will be achieved 90% of the time.

In any case, a supplemental injection is necessary when the mandibular block or infiltration fails to sufficiently anesthetize the site of the disease. Known means of supplying supplemental injections of an anesthetic are by periodontal ligament injection and intraosseous injection. When the mandibular block or infiltration anesthesia is not sufficiently effective, the periodontal ligament injection is usually the next choice. This injection is usually given with a device that improves the mechanical advantage over that of an ordinary syringe, known as the ligamental gun syringe, with an extra short, 30 gauge needle. The bevel of the needle is placed against the root of the tooth while it is advanced down along the gingival pocket into the periodontal ligament space until resistance is met. The anesthetic is delivered to this location. This process suffers from having a short effective period of the anesthesia and the process poses a risk of osteomyelitis.

The other choice is intraosseous injection, by which local anesthetic is injected directly into the cancellous bone of the alveolar process surrounding the root of the targeted tooth. This method is ideally suited to treatment of mandibular teeth because it provides for perforation of the thick mandibular cortex, prior to injection of the anesthetic. Generally, at some position immediately adjacent the affected tooth a small perforation is made in the cortex of the alveolar process at a location which will allow the anesthetic to be delivered into the inner compartment composed of spongiosa or medullary (cancellous) bone. If the perforation is correctly located, the patient feels immediate relief from pain and, depending on the location of the perforation and the quantity of anesthetic delivered, the anesthesia may affect one or several teeth, as needed.

The effectiveness of the intraosseous injection was reported in the following study: Nustein, J., Reader, A., and Nist, R., "Anesthetic Efficacy of the Supplemental Intraosseous Injection of 2% Lidocaine with 1:100,000 Epinephrine in Irreversible Pulpitis", *Journal of Endodontics*, (1998, 24:287). The Nustein et al. study included data showing that 81% of mandibular teeth required intraosseous anesthesia due to the irreversible pulpitis present and failure of the traditional mandibular block. Regarding maxillary teeth, the data showed that the intraosseous injection was required in 12% of the teeth. Overall the intraosseous injection was successful in 88% of the cases, thereby achieving the pulpal anesthesia necessary for endodontic treatment. A similar study (Parente, S., Anderson, R., Herman, W. "Anesthetic Efficacy of the Supplemental Intraosseous Injection for Teeth with Irreversible Pulpitis", *Journal of Endodontics*, (1998, 24:826)) revealed a 91% success rate of intraosseous injections thus allowing endodontic therapy.

Types of intraosseous injections vary. One form of intraosseous injection is the Stabident System by Fairfax, Dental, Inc. (See http://www.stabident.com/delivery-systems-described-regular.html citing U.S. Pat. Nos. 5,057,013 and 5,173,050 to Dillon issued on Oct. 15, 1991 and Dec. 22, 1992, respectively, for a "Dental Cortical Plate Perforator"), which uses a two-step perforation and injection process. This Stabident two-step procedure is referenced in the Parente study, supra, as well as an article by Ronald Brown, DDS, MS, "Intraosseous Anesthesia: A Review", *Journal of the California Dental Association*, (October 1999). Specifically, the Stabident System consists of using a perforator (0.9 mm long with a 0.43 mm diameter) to drill hole in the cortical plate of the alveolar process and a separate injection needle (27 gauge) to inject the anesthetic into the cancellous bone within. The injection needle attaches to a separate standard syringe. Kits are available with injection needles modified such that the bevel at the end of the needle has a blunted tip. Generally, the site of a lateral injection for this system is a point about 2 mm apical to the intersection of a horizontal line along the gingival margins of the teeth and a vertical line through the interdental papilla. Unfortunately, this two-step Stabident process presents a risk of damaging the bone while drilling and a risk of drilling into the root surface of the tooth. In addition to the risk of injury to the patient, bleeding and clotting at the drilling site impair the view of the drill point, making precise drilling more difficult and obscuring the opening during the second step of injecting the anesthetic. Furthermore, in a case of periodontal gingival disease, a drill hole cannot be made in the area to be injected.

An improvement over the two-step intraosseous injection process is described in U.S. Pat. No. 3,976,070 to Dumont, issued on Aug. 24, 1976, which claims a support device for a small gauge hypodermic needle that allows the injection to be completed in a one-step process. The support device includes a funnel-like structure adapted to fit over the base of the hypodermic needle and a siding tip guard adapted to slide coaxially inside the funnel-like structure in the manner of an expansible telescope. At the end of the tip guard, away from the funnel-like structure, there is an enlarged hub adapted to press against the gum in the mouth of the patient and through which the hypodermic needle is inserted, through the gum and into the bony structure below. This one-step intraosseous needle eliminates the problems associated with the two-step process. The small size of the needle reduces the risk of damage to the bone and the underlying tooth, even if the site for the injection is not accurately located. The proper location for the injection is visually selected at a approximately 1 mm above the alveolar crest of a maxillary tooth or 1 mm below the aveolar crest of a mandibular tooth.

As discussed above, the primary advantage of intraosseous injections is the targeted administration of a local anesthetic to one or several particular teeth. While a slight miscalculation of the perforation and injection site when using the Dumont '070 system will not result in damage to the bone or underlying tooth, it will likely make the anesthetic ineffective on the area where it is needed. Therefore, correct positioning of the needle for perforation and injection is crucial. Traditionally, the needle is position at the site of injection by viewing the area and simply estimating the correct insertion point. In order for the anesthetic to be effective using the system disclosed in the Dumont '070 patent, the needle must perforate the cortex approximately 1 mm from the aveolar crest, as described above. However, even if the correct perforation location is selected, the needle may bend, buckle, and/or slide along the cortex rather than penetrating the precise selected location. This bending and/or sliding of the needle may cause a distorted infusion of the anesthetic and an ineffective injection.

In order for the injection to be most effective, the anesthetic must be delivered to the cancellous bone of the alveolar process adjacent the affected root. As described above, the needle must be inserted through the outer cortical plate into this cancellous bone. The needle should not penetrate beyond the cancellous bone through the inner cortical plate or alveolar bone into the root of the tooth. Again, the proper depth for the site of the injection is estimated by viewing the area where the injection is to be made. This "by sight" method of aligning the syringe with the targeted injection site and for determining the depth of the injection is not as precise as it should be given the resultant ineffectiveness of the anesthetic if an error does occur.

Thus, there is a need for an improved one-step intraosseous injection system. It would be advantageous over the prior art if the system was configured for attachment to a standard syringe. It would also be advantageous if the system simply and economically reinforced and stabilized the injection needle during bone penetration, promoted accurate targeting of injections, and included a means for limiting the depth of injection needle penetration. Specifically, it would be advantageous over the prior art to: (1) configure a intraosseous injection needle for attachment onto a standard syringe (i.e. a dental anesthetic syringe having a short high tensile strength needle); (2) provide the injection needle with a protective sliding cannula and sleeve to prevent bending and sliding of the injection needle during penetration of cortical bone (i.e. the outer cortical plate of the alveolar process); (3) attach a sight/gauge to the sleeve for targeting the precise position of penetration and insertion of the injection needle into the bone (i.e. the alveolar process); and, (4) incorporate a cannula stop in the sleeve which effectively limits penetration of the injection needle, ensuring delivery of the injected substance to the targeted location (i.e. cancellous bone).

SUMMARY OF THE INVENTION

It is the primary object of the present invention to provide an improved intraosseous injection system configured for attachment onto a standard syringe.

It is another object of the present invention that the intraosseous injection system includes a short, high-tensile strength, hypodermic injection needle.

It is yet another object to of the present invention to circumscribe the injection needle by a cannula and protective sleeve with the cannula partially inserted into the sleeve and whereby the cannula and sleeve provide improved support and protection of the intraosseous injection needle such that the needle possesses sufficient rigidity to prevent bending, buckling and sliding during penetration of cortical bone.

It is another object of the present invention that the protective sleeve includes a sight/gauge to assist in targeting a specific injection site and an integrated cannula stop limiting the retraction of the cannula into the sleeve and thereby limiting the depth of penetration of the injection needle into the bone.

Lastly, it is an object of the present invention that the improved intraosseous injection system is especially suited for intraosseous pulpal anesthesia (a.k.a. injection of a local anesthetic into the cancellous bone of the alveolar process surrounding a targeted tooth that requires anesthesia prior to endodontic treatment). The system is configured for attachment onto a standard dental anesthetic syringe with a short, high tensile strength, injection needle that is supported by a cannula and sleeve, such that the needle is able to penetrate the outer cortical plate of the alveolar process without bending, buckling or sliding. The system further includes a sight/gauge on the sleeve for locating the precise location along the alveolar process for penetration of the injection needle and a cannula stop within the sleeve limiting the depth of injection into the alveolar process. Specifically, the stop prevents the injection needle from passing through the cancellous bone into the inner cortical plate, alveolar bone, or root of the targeted tooth.

According to the stated objects, the present invention is an improved intraosseous injection system for pulpal anesthesia adapted to attach onto a standard dental anesthetic syringe. The system uses a high-tensile strength, hypodermic injection needle mounted within and protected by a cannula, sleeve with a reinforcing stabilizer, and hub.

The cannula, sleeve with a reinforcing stabilizer and hub are each rigid, hollow, and essentially cylindrical having open distal and proximal ends through which the length of the needle extends from its distal to proximal end. The proximal end of the hub is threaded for screw mounting onto the dental syringe. The proximal end of the needle extends slightly beyond the proximal end of hub to allow the needle to penetrate a reservoir of anesthetic within the syringe when the hub is threaded thereon. The distal end of the hub is attached by some means to the proximal end of the sleeve.

The junction between the hub and sleeve includes a fixed barrier with a through bore for supporting the needle centrally within the sleeve and hub. The sleeve tapers to its distal end which includes a reinforcing stabilizer where the proximal end of the cannula is partially and retractably engaged and slideably supported therein. The inner diameter of the cannula is sized to circumscribe the needle and thus support the needle. The reinforcing stabilizer of the distal end of the sleeve is sized to circumscribe the cannula and thus frictionally supports the cannula.

A stop is formed inside the sleeve to limit the retraction of the cannula within the sleeve. The distal end of the needle extends beyond the distal end of a fully retracted (stopped) cannula to a length equal to the desired depth of penetration into the bone.

An outwardly extending combination sight and measuring gauge (sight/gauge) is mounted on the outer surface of the tapered distal end of the sleeve for sighting and measuring the correct location to administer an injection. The sight/gauge is triangular or rectangular in shape. The sight/gauge may be marked with indicia and/or ruler markings (i.e. mm). The top point of the gauge is for use as the sight for visually locating precise injection site.

The distal end of the needle is formed with a rounded bevel to prevent tearing of tissue and clogging.

The needle is further coated with silicon material to reduce friction upon penetration.

BRIEF DESCRIPTION OF THE DRAWINGS

Other objects, features, and advantages of the present invention will become more apparent from the following detailed description of the preferred embodiment and certain modifications thereof when taken together with the accompanying drawings in which.

DETAILED DESCRIPTION OF THE PREFERRED EMBODIMENTS

The present invention 100 is an improved intraosseous injection system. The invention is described herein with respect to intraosseous injection of anesthetic into mandibular or maxillary alveolar process cancellous bone for providing anesthesia to an affected tooth (teeth) during endodontic treatment. However, those skilled in the art will recognize that this system may be suitable for other types of intraosseous injections, including injections of non-anesthetic substances or injections of substances into other bone sites.

Figure 1:
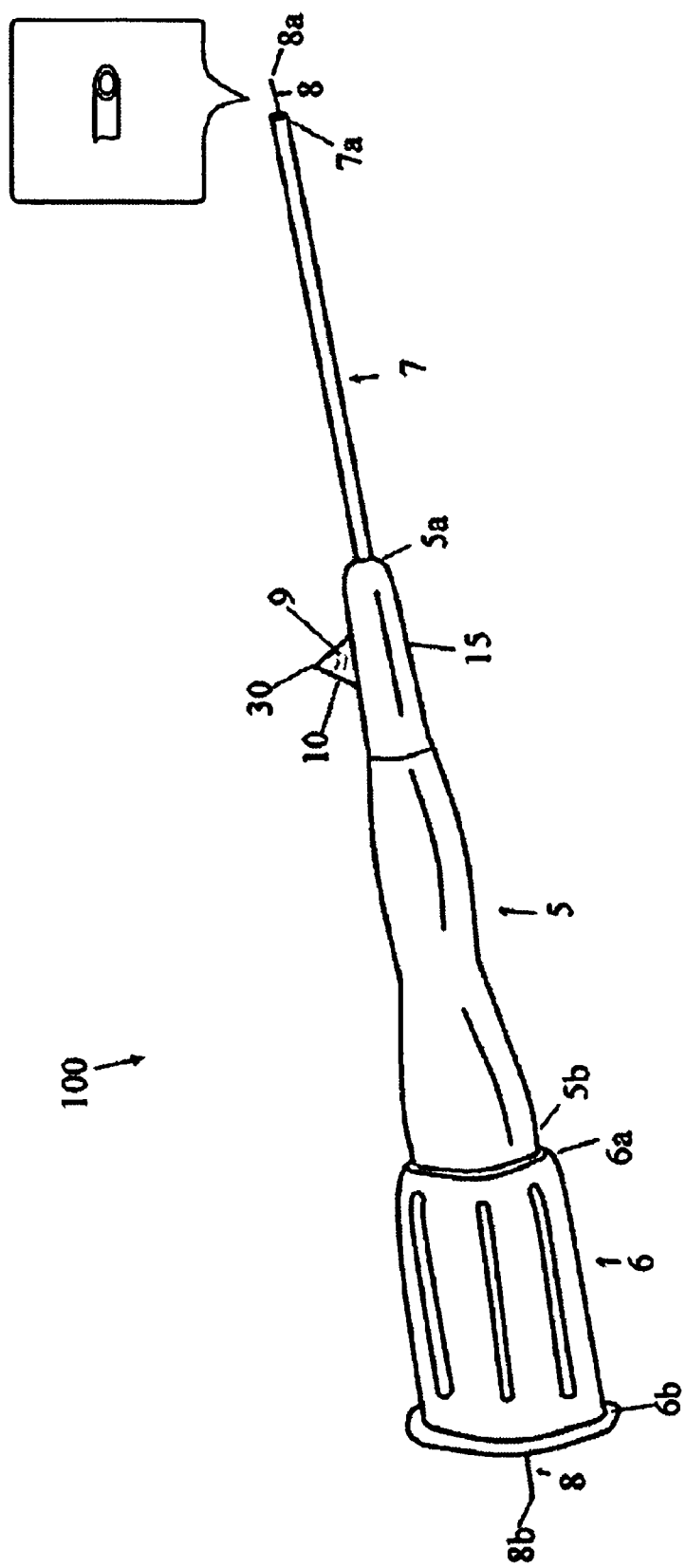
FIG. 1 is a perspective of the device of the present invention with the cannula retracted, including an exploded view of the rounded bevel of the injection needle.
Figure 3:
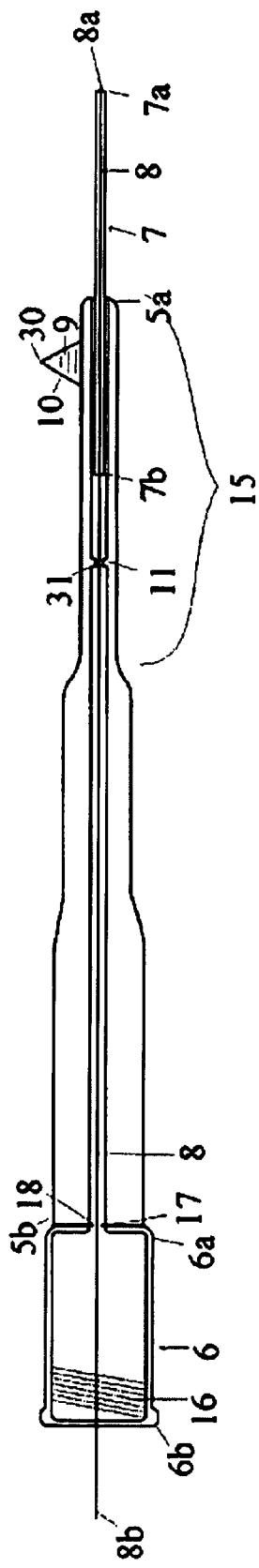
FIG. 3 is a cross-sectional view of the device, as shown in FIG. 1, with the cannula fully extended.
Figure 2:
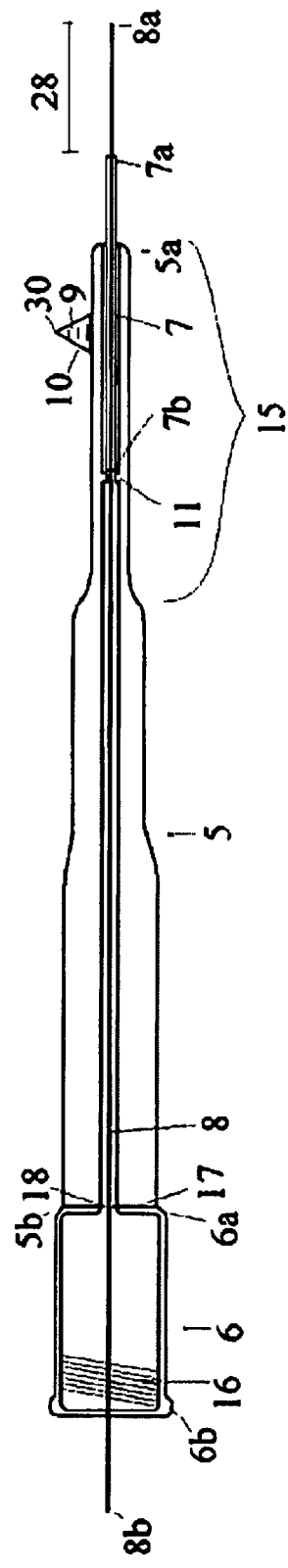
FIG. 2 is a cross-sectional view of the device as shown in FIG. 1, with the cannula fully retracted.

The intraosseous injection system 100 is a device that simply and economically incorporates a standard syringe (i.e. dental anesthetic syringe) into an improved one-step system that provides greater support for intraosseous injection needles during penetration of cortical bone while simultaneously providing a means for accurately targeting injection sites and limiting injection depth. Referring in combination to FIGS. 1–3, the intraosseous injection system 100 of the present invention uses a high-tensile strength, hypodermic injection needle 8 mounted within and protected by a rigid cannula 7, a sleeve 5 with a reinforcing stabilizer 15, and a hub 6.

The cannula 7, sleeve 5 with reinforcing stabilizer 15, and hub 6 are each rigid, hollow, and essentially cylindrical in shape. The cannula 7, sleeve 5 with reinforcing stabilizer 15 and hub 6 each have open distal and proximal ends (7a–b, 5a–b, and 6a–b, respectively) integrally-joined end-to-end to form a passage there through, through which the length of the needle 8 extends from its distal to proximal end (8a–b). As seen in FIG. 3, the inner surface of the proximal end of the hub 6b is preferably threaded 16 for screw mounting onto a standard syringe (not shown) which wields the high-tensile strength, hypodermic injection needle 8. The proximal end of the needle 8b extends slightly beyond the proximal end of hub 6b to allow the needle 8 to penetrate a reservoir of anesthetic within the syringe when the hub 6 is threaded thereon. The distal end of the hub 6a is attached by suitable means to the proximal end of the sleeve 5b (i.e. welded, integrally molded, etc.). The junction between the hub 6 and sleeve 5 includes a divider 17 with a through bore 18 for supporting the needle 8 centrally within the sleeve 5 and hub 6. The sleeve 5 is tapered at its distal end 5a. The distal end of the sleeve 5a is comprised of a reinforcing stabilizer 15 formed of metal or plastic, either attached to or integrally molded with the rest of the sleeve 5, for supporting the needle 8 within cannula 7. The proximal end 7b of the cannula 7 is slideably supported lengthwise within the hollow distal end of the sleeve 5a (within reinforcing stabilizer 15).

The inner diameter of the cannula 7 is sized to just circumscribe the needle 8 and thus support the needle 8. The reinforcing stabilizer 15 of the distal end of the sleeve 5a is sized to just circumscribe the cannula 7 and thus frictionally supports the cannula 7. Referring to FIG. 3, when the device 100 is not in use, the cannula 7 is fully extend and thus protects and supports the distal end of the needle 8a. As the needle 8 is placed at the injection site and pressure is exerted to begin penetration, the cannula 7 (which does not penetrate the injection site) slides (retracts) against frictional forces further inside the sleeve 5.

A stop 11 is formed inside the sleeve 7, and particularly inside reinforcing stabilizer 15, to limit the retraction of the cannula 7 within the sleeve 5. The needle 8 passes through appropriately channel 31 that circumscribes and further supports the needle 8. The distal end of the needle 8a extends beyond the distal end 7a of a fully retracted cannula 7 a predetermined length (l) 18. The predetermined length (l) should be set such that it is equal to the desired depth of penetration of the cortical bone into cancellous bone, plus the depth of any other tissue (i.e. gingiva) that must be penetrated prior to reaching the bone. The user will begin the injection by inserting the needle 8 at the targeted injection site. The distal edge of the cannula 7a abuts the outermost tissue surface and begins to retract into the sleeve (against frictional forces) as the needle 8 penetrates the bone. When the cannula 7 reaches the stop 11 and can no longer retract, the predetermined injection depth is met and the substance contained in the syringe may be injected. See below discussion of FIGS. 3 and 4 for further explanation of the operation of the present invention specifically related to intraosseous injections of anesthetics during endodontic treatment.

An outwardly protruding combination sight and measuring gauge (sight/gauge) 10 is mounted on the outer surface of the tapered distal end of the sleeve 5a (the reinforcing stabilizer 15) for sighting and measuring the correct location to administer an injection. The sight/gauge 10 may be either triangular or rectangular in shape. The sight/gauge 10 may be marked with indicia and/or ruler markings 9 (i.e. mm) for measuring the precise injection site. Ideally, the uppermost edge 30 of the sight/gauge 10 is used as the sight for visually aligning the needle up with the precise injection site.

The injection needle 8 is preferably constructed of high strength material to resist bending and buckling when penetrating cortical bone and is formed with a rounded bevel 31 at distal end 8a to prevent tearing of tissue and clogging of the needle 8 (See explosive view within FIG. 1). The injection needle 8 may be further coated with silicon material to reduce friction upon penetration into the cortical bone.

As stated above, the present invention is particularly suited for intraosseous injections of anesthetics for endodontic treatment.

Figure 4:
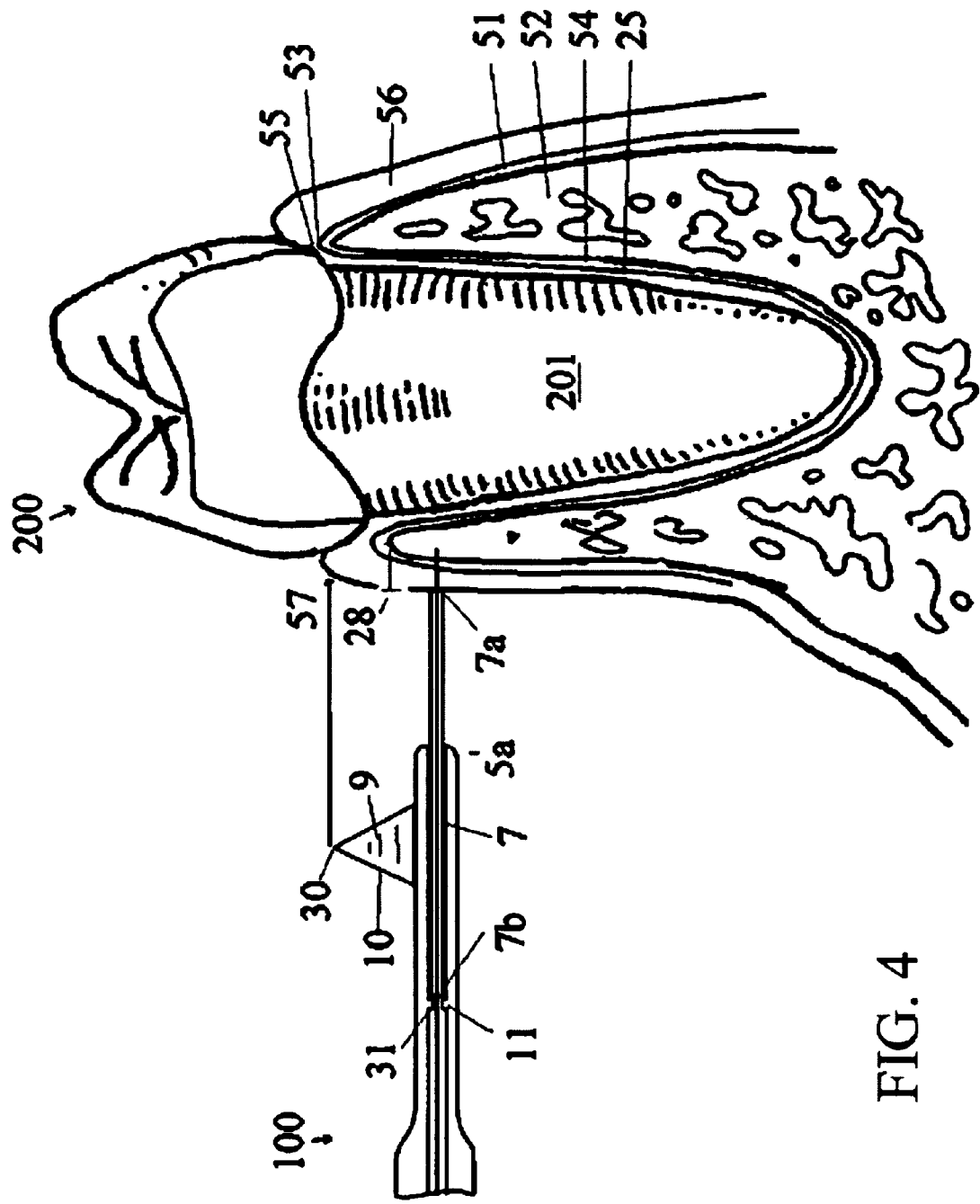
FIG. 4 is a cross-sectional, operational illustration of the device of the present invention used to provide anesthesia to a mandibular tooth.

FIG. 4 illustrates the device of the present invention 100 in use, providing anesthesia to a mandibular tooth. FIG. 4 further particularly illustrates a mandibular tooth 40 embedded in the mandibular alveolar process 50 and held in place by the periodontal ligaments 25. The alveolar process 50 is made up of outer cortical plates 51, the spongy cancellous bone 52, and the alveolar bone 54 (inner cortical plate consisting of a thin layer of compact bone that forms the tooth socket). The rim of the alveolar bone 54 forms the alveolar crest 53 and is positioned essentially parallel to the cementum/enamel junction 55. The outer cortical plate 51 is covered by gingiva 56 which connects with the periodontal ligaments 25 at the alveolar crest 53. The average depth of the outer cortical plate 51 ranges from approximately 2.0 mm (premolars) to 3.0 mm (molars) (See Denio, D., Torabinejad, M., and Bakland, L., "Anatomical Relationships of the Mandibular Canal to its Surrounding Structures in Mature Mandibles", *J. Endo* 1992; 18:161) and the depth of the attached gingiva from the alveolar crest 53 to the gingival margin 57 (margin between gingival 56 and tooth 200) is approximately 2 mm (See Glickman, I., *Clinical Periontology* 2$^{nd}$ *Ed.*, W. B. Saunders, (1958). As discussed above, anesthetics are most effective when injected into the cancellous bone 52 adjacent the affected tooth.

Consequently, in order to ensure that the injection is made into the alveolar process cancellous bone 52, the needle 8 should extend beyond the distal end of the cannula 7a (when retracted) approximately 3.5–4 mm. Those skilled in the art will recognize that the distance a needle 8 extends beyond the cannula 7 may be altered any number of ways, including using needles 8 of differing lengths, using cannulas 7 of differing lengths or altering the position of the stop 11 (i.e. by a slide and lock mechanism).

The hub 6 of device 100 is provided with a threaded inner surface 16 (see FIG. 2) compatible with metric or imperial coding system for attachment to a standard dental syringe (not shown). The hub 6 is screw mounted onto the dental syringe and tightened such that the sight/gauge 10 is positioned to point upward when injecting mandibular teeth and downward when injecting maxillary teeth. The needle 8 is a standard 25, 27, or 30 gauge needle and will extend beyond the proximal end of the hub 6b a standard distance of approximately 12 mm, thereby allowing the needle to connect with the reservoir of anesthetic within the dental syringe.

For effective administration of anesthetics using this system, the needle 8 should perforate the cortex 51 approximately 1 mm above the aveolar crest of a maxillary tooth or approximately 1 mm below the aveolar crest 53 of a mandibular tooth. Taking into account these requirements and the fact that the average depth of the gingiva 56 from the alveolar crest 53 to the gingival margin 57 is 2.0 mm, the ideal height for the sight/gauge 10 is approximately 3 mm with ruler markings or indicia 9 indicating millimeters.

Prior to use, it is intended that the intraosseous injection needle 8 is protected and supported by the cannula 7 in an extended position, such that the distal end of said needle 8a does not extend beyond the cannula 7. The cannula 7 is preferably formed of a hollow stainless steel cylinder with a circular cross section, to reinforce and stabilize the needle 8. Again referring to FIG. 4, in operation the distal end of the needle 8a is pointed at the gingiva 56 covering the root area 201 of the affected tooth 200. By sighting along the sleeve 5 and across the uppermost edge 30 of the sight/gauge 10, the position of the injection needle 8 can be adjusted until the uppermost edge 30 is in line with the gingiva 56/tooth 200 margin 57. The cannula 7 abuts the gingiva 56 and the injection needle 8 can then be advanced and inserted while maintaining the alignment of the edge 30 with the gingiva/tooth margin 57. The 3.0 mm sight/gauge 10 will place the point of injection 1.0 mm below the aveolar crest 53 for a mandibular tooth (1.0 mm above the aveolar crest for a maxillary tooth). As pressure is applied to insert the needle 8 and the needle 8 penetrates the cortical bone 51, the cannula 7 remains abutted against the gingiva 56 and retracts into sleeve 5, stopping at stop 11. Once the retraction of the cannula 7 stops, further advance of the needle 8 is prevented and the correct depth of penetration into the cancellous bone is met. Proper penetration depth ensures that damage is not caused by penetration of the alveolar bone 54 or root 57 and optimizes the effectiveness of the anesthetic.

In the preferred embodiment, to accommodate this 3.5–4.0 mm penetration depth into the alveolar process and the 12 mm extension of the needle beyond the proximal end of the hub 6b, the needle 8 should be approximately 48 mm end to end. Additionally, the cannula 7 in its retracted position should extend approximately 2–3 mm beyond the distal end of the sleeve 5a and in its retracted position should extend approximately 5–7 mm there from.

It is contemplated that, in preparation for endodontic therapy on a particular tooth, two injections will be made. One injection will be made on each side of the affected tooth into the lingual and facial cortical plates, respectively. The improved intraosseous injection system 100 disclosed herein may be used to locate the correct position of needle for both injections sites.

As stated above, FIG. 4 illustrates the operation of the device 100 on a mandibular tooth 200. However, simply by rotating the screw mounted hub 6 180 degrees so that the sight/gauge 10 points downward in relation to normal dental syringe positioning for maxillary injections, the device 100 will operate the same for a maxillary tooth.

The advantages of the present invention include (1) specific targeting of the proper injection site, (2) a means to adequately limit the depth of an injection, and (3) added support and protection for the injection needle. Each of these benefits will help to optimize the effectiveness of an injected substance.

Having now fully set forth the preferred embodiments and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

I claim:

1. An intraosseous injection system comprising:
   a sleeve having a proximal end and a distal end;
   a hub mounted on the proximal end of the sleeve for attachment to a standard syringe;
   a cannula slidably supported lengthwise in the distal end of said sleeve for retraction therein;
   a syringe attached to said hub, said syringe including a hypodermic needle extending through the sleeve and cannula;
   a stop formed inside said sleeve to limit retraction of said cannula; and
   a sight mounted on said sleeve for sighting a correct location to administer an injection of anesthetic from said syringe.

2. The intraosseous injection system according to claim 1, further comprising a divider in said sleeve having an aperture for supporting the needle centrally therein.

3. The intraosseous injection system according to claim 1, wherein said sleeve comprises a rigid sleeve having a proximal end and a tapered distal end.

4. The improved intraosseous injection system according to claim 1, wherein said hub comprises a threaded hub for screw-attachment to said syringe.

5. The intraosseous injection system of claim 1 wherein the needle is provided with a rounded bevel.

6. The intraosseous injection system of claim 1 wherein the needle is silicon coated.

7. The intraosseous injection system of claim 1 wherein said sight further comprises an outwardly protruding measuring gauge.

8. The intraosseous injection system of claim 7 wherein said measuring gauge protrudes outward from said sleeve by a distance within a range of from approximately 2–4 mm.

9. The intraosseous injection system of claim 8 wherein said measuring gauge is marked with measuring indicia along its outwardly protruding extent.

10. The intraosseous injection system of claim 1 wherein the stop inside the sleeve is positioned to prevent further retraction of the cannula at a point where the exposed length of needle, beyond the end of the cannula is approximately 2–3 mm.

11. The intraosseous injection system of claim 1 wherein said sleeve further comprises a reinforcing stabilizer for reinforcing said cannula lengthwise.

12. The system of claim 7, wherein said cannula further comprises a hollow body with an interior diameter sized to circumscribe said needle, and said reinforcing stabilizer has an interior diameter sized to circumscribe said cannula.

13. The system of claim 1, wherein said system is used for intraosseous injections into the cancellous bone of the mandibular or maxilliary alveolar process for providing anesthesia for endodontic treatment.

14. The system of claim 13, wherein said injections are of anesthetics.

15. The system of claim 4, wherein said hub is screw mounted onto a standard dental syringe.

16. The system of claim 15, wherein said needle extends a predetermined distance beyond said hub to allow the needle to penetrate a reservoir of anesthetics within the mounted dental syringe.

17. The system of claim 16, wherein the needle extends approximately 12 mm beyond said hub.

18. The system of claim 9, wherein said needle extends beyond the cannula, when said cannula is retracted to the cannula stop by a distance of approximately 3.5–4.0 mm.

19. The system of claim 4, wherein screw mounting said hub on said dental syringe such that the sight/gauge is oriented pointing upward relative to the normal operating position of the syringe configures the system for mandibular injections, and screw mounting said hub on said dental syringe such that the sight/gauge is oriented pointing downward relative to the normal operating position of the syringe configures the system for maxillary injections.

20. A method for using an intraosseous injection system having a syringe with a needle extending lengthwise through a cannula, sleeve and hub, said cannula partially and retractably mounted within said sleeve, said sleeve attached to said hub and including an internal cannula stop and outer sight, and said hub having a threaded internal surface for screw mounting said system onto a standard syringe; said method comprising the steps of:
   targeting an injection site using the sight;
   placing the cannula against the targeted injection site with said needle retracted in said cannula;
   applying pressure to insert said needle into the injection site, through cortical bone and into cancellous bone, said pressure simultaneously causing the cannula abutting said injection site to retract within said sleeve until stopped by the cannula stop and thereby preventing the needle from penetrating deeper; and,
   operating the syringe to inject the substance held in the reservoir into the bone.

* * * * *